United States Patent [19]

Southren et al.

[11] Patent Number: 4,863,912
[45] Date of Patent: Sep. 5, 1989

[54] USE OF TETRAHYDROCORTISOL IN GLAUCOMA THERAPY

[75] Inventors: Aaron L. Southren; Bernard I. Weinstein; Gary G. Gordon, all of Valhalla, N.Y.

[73] Assignee: New York Medical College, Valhalla, N.Y.

[21] Appl. No.: 864,610

[22] Filed: May 19, 1986

[51] Int. Cl.$^4$ .............................................. A61K 31/56
[52] U.S. Cl. .................................. 514/177; 514/178; 514/182; 514/913; 514/914
[58] Field of Search ............... 514/177, 178, 182, 913, 514/914

[56] References Cited

U.S. PATENT DOCUMENTS 2,783,226  2/1957  Gould et al. .................. 260/397.47

OTHER PUBLICATIONS

Chemical Abstracts, vol. 88 (1978), #99603a; Halatek et al.
Chemical Abstracts, vol. 90 (1979); 198072z, Gierkowa et al.
Meyer et al., "Influence of Norethynodrel with Mestranol on Intraocular Pressure in Glaucoma", *Arch Ophthal*, vol. 75, Jun. 1966.
Treister et al., "Intraocular Pressure and Outflow Facility", *Arch. Ophthal*, vol. 83, Mar. 1970.
Lamble et al., "Some Effects of Progestogens, Oestrogens and Androgens on the Ocular Tension of Rabbits and Owl Monkeys", *Exp. Eye Res.*, 26, 599–610, (1978).
Southren, et al., "5-beta-dihydrocortisol: Possible Mediator of the Ocular Hypertension in Glaucoma", *Investigative Ophthalmology & Visual Science*, Mar. 1985, vol. 26, pp. 393–395.
Crum, et al., "A New Class of Steroids Inhibits Angiogenesis in the Presence of Heparin or a Heparin Fragment", *Science*, Dec. 20, 1985, vol. 230, pp. 1375–1378.

*Primary Examiner*—Douglas W. Robinson
*Assistant Examiner*—Joseph A. Lipovsky
*Attorney, Agent, or Firm*—Zarley, McKee, Thomte, Voorhees & Sease

[57] ABSTRACT

Pharmaceutical compositions comprising tetrahydrocortisol and method of using same in the control of intraocular pressure are disclosed.

7 Claims, 1 Drawing Sheet

USE OF TETRAHYDROCORTISOL IN GLAUCOMA THERAPY

BACKGROUND OF THE INVENTION

This invention relates to a method and compositions useful in controlling intraocular pressure. Specifically, this invention relates to compositions comprising tetrahydrocortisol; and methods of treatment comprising administering these compositions to treat ocular hypertension, including the glaucoma syndrome.

Tetrahydrocortisol is a normal cortisol metabolite found in urine and serum of normal humans but not in Trabecular Meshwork (TM) cells isolated from normal eyes. Cortisol is metabolized only slowly by normal TM cells. However, in TM cells from primary open angle glaucoma (POAG) patients, the rate limiting enzyme delta-4-reductase is aberrantly hyperexpressed and the activity of the 3-oxidoreductase is reduced. This enzyme imbalance leads to the accumulation of 5-alpha and 5-beta-dihydrocortisol in POAG TM cells.

While applicant is bound by no theory, it is postulated that 5-beta-dihydrocortisol is toxic to TM cells and compromises TM function. Since the trabecular meshwork is the major site for resistance to aqueous humor outflow, compromised TM function may lead to an increase in intraocular pressure. It is believed that tetrahydrocortisol may antagonize the action of 5-alpha and/or 5-beta-dihydrocortisol, in a yet to be defined manner, and that it also may function as an inhibitor of A-ring reductase activity.

Thus, it is a primary objective of the present invention to provide methods of treatment and pharmaceutical compositions which will control ocular hypertension, including retarding or delaying the progressive field of vision loss associated with glaucoma, by using tetrahydrocortisol.

Another objective of the present invention is to provide pharmaceutical compositions containing tetrahydrocortisol for topical treatment of glaucoma.

Another primary objective of the present invention is to provide pharmaceutical compositions which may be dosed topically, with the compositions being suitable for delivery in dose form in topical drops, in ophthalmic gels, and in other optically suitable dosage forms, such as ophthalmic suspensions and intracameral delivery systems.

SUMMARY OF THE INVENTION

Intraocular pressure of affected eyes is reduced by topically administering an intraocular pressure lowering effective amount of tetrahydrocortisol. Pharmaceutical compositions containing tetrahydrocortisol may be gels, ointments, suspensions or other suitable ophthalmic delivery systems. While any of the stereoisomers of tetrahydrocortisol are suitably active, the most preferred stereoisomers are 3-alpha, 5-beta and 3-alpha, 5-alpha.

DETAILED DESCRIPTION OF THE INVENTION

Figure 1:
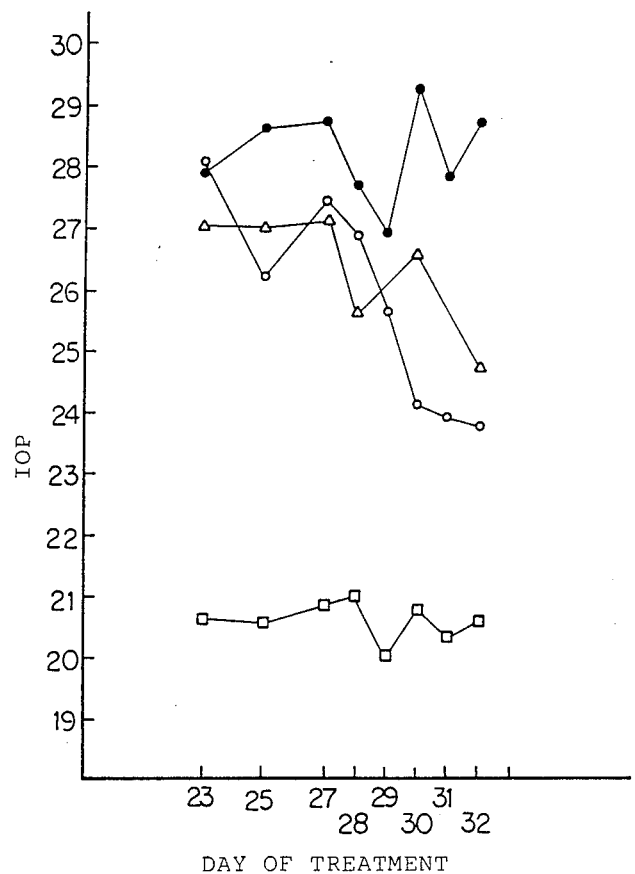
FIG. 1 shows a plot comparing a control, and treated affected eyes so that one may compare under comparable conditions the intraocular pressure of affected eyes before and after treatment.

Tetrahydrocortisol (I) is a known compound. It has a molecular weight of 366.5, and an emperical formula of $C_{21}H_{34}O_5$. The compound is commercially available and may for example be obtained from Research Plus, Inc., Post Office Box 324, Bayonne, N.J. It may also be synthesized if desired. The general approach to synthesis involves treating tetrahydrocortisol acetate with semicarbazide to form 20-semi-carbazone. This is dissolved in solution and reduced to potassium borohydride. It is then suspended in methylene chloride and treated with hydrochloric acid. The product is stable at room temperature and requires no extraordinary storage precautions. Tetrahydrocortisol (I) has the following formula:

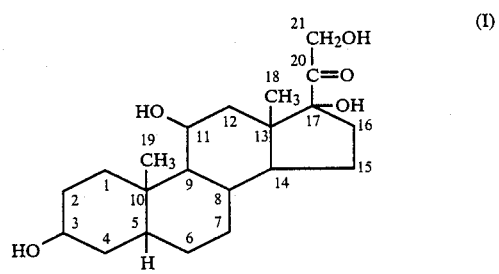

Tetrahydrocortisol may exist in several stereoisomeric forms. All of the stereoisomeric forms are active. Specifically, with regard to stereoisometry, for tetrahydrocortisol (I) it refers to relative positions of hydroxyl group and hydrogen group at the 3,5 position, as to whether or not they are above or below the plane of the ring structure. Alpha position refers to above the plane of the ring structure, and beta refers to below the ring structure. Thus, tetrahydrocortisol may exist as 3-alpha, 5-beta; 3-alpha, 5-alpha; 3-beta, 5-alpha; and 3-beta, 5-beta. The preferred isomer of structure (I) for use in this invention is 3-alpha, 5-beta-tetrahydrocortisol. The ring containing the 1-5 positions is referred to as the "A-ring."

The ophthalmically active tetrahydrocortisol (I) may be incorporated into various types of ophthalmic formulations for delivery to the eye. For example, (I) may be combined with ophthalmologically acceptable preservatives, surfactants, viscosity enhancers, buffers, sodium chloride and water to form an aqueous, sterile ophthalmic suspension. In order to prepare sterile ophthalmic ointment formulations, the active ingredient is combined with a preservative in an appropriate vehicle, such as, mineral oil, liquid lanolin, or white petrolatum. Sterile ophthalmic gel formulations may be prepared by suspending the active ingredient in a hydrophilic base prepared from the combination of Carbopol-940 (a carboxy vinyl polymer available from the B.F. Goodrich Company) according to published formulations for analogous ophthalmic preparations; preservatives and tonicity agents can be incorporated. The specific type of formulation selected will depend on various factors, such as, the type of ophthalmic hypertension, being treated and dosage frequency. Ophthalmic suspensions, ointments and gels are the preferred dosage forms. The steroid (I) will normally be contained in these formulations in an amount of from about 0.05% to about 5.0% by weight, preferably from about 0.5% to about 3.0% by weight. Thus, for topical presentation these formulations would be delivered in modest excess to the surface of the eye 1-4 times/day depending upon the discretion of the clinician. While preservatives are normally recommended for multi-dose containers, their presence is not critical. Pharmaceutical compositions of the present invention designed for single use do not require any preservative.

The formulations set out below illustrate the dosage forms which may be utilized in the present invention. In these formulations, the term tetrahydrocortisol represents any of the above-described stereoisomers of Structure I, and especially includes the preferred stereoisomer 3-alpha, 5-beta-tetrahydrocortisol.

| Suspension | Composition % W/W |
|---|---|
| Tetrahydrocortisol (I) | 0.05-5.0 |
| Benzalkonium Chloride | 0.001-0.002 |
| Polysorbate 80 or Tyloxopol | 0.01-1.0 |
| Phosphate buffer pH | 5 mMol-100 mMol |
| Sodium Chloride | 0-0.9 |
| Hydroxypropyl methylcellulose | 0.1-0.5 |
| Water to produce 100 parts by weight | Balance |

| Ointment | Composition % W/W |
|---|---|
| Tetrahydrocortisol (I) | 0.05-5.0 |
| Chlorobutanol | 0.5 |
| Methyl or Propyl Parabens | 0.01-0.1 |
| Mineral Oil | 0-10 |
| Liquid Lanolin | 0-10 |
| White petrolatum to produce 100 parts by weight | Balance |

| Gel | Composition % W/W |
|---|---|
| Tetrahydrocortisol (I) | 0.05-5.0 |
| Carbopol 940 | 1-4 |
| Sodium hydroxide | q.s. (pH: 4.5-8.0) |
| Sodium chloride | 0-0.9 |
| Water q.s. | Balance |

The treatment method of the present invention comprises application of an effective amount of the active form of Structure (I) to the eye when indicated for control of intraocular pressure. The dosage regimen utilized will depend on various factors, such as, the patient's age, sex, weight and history and magnitude of the intraocular pressure deviation from the normal. In general, the above-described formulations may be topically applied, for example, as drops to the upper globe, or as a 0.5-1 cm strip of ointment or gel to the lower conjunctival sac of the eye. Suspensions will generally be applied 1 to 4 times daily, while ointments or gels will generally be applied once or twice daily. The application of sustained release formulations (e.g., polymer based gels) once daily at bedtime will be preferred in some conditions.

The following examples are offered to illustrate but not limit the process of the present invention. In the examples, the activity of tetrahydrocortisol (I) was tested in vitro in rabbits. It is known that rabbit eye models correlate and predict human eye testing.

EXAMPLES

Recent studies have shown that young rabbits are more consistently sensitive to the ocular hypertensive effect of topical glucocorticoids. 5-beta-dihydrocortisol can potentiate the IOP (intraocular pressure) raising effect of topically applied dexamethasone. This potentiated rabbit model, using 5-beta-dihydrocortisol is particularly appropriate in evaluating antiglaucoma agents since this metabolite has been shown to accumulate in cultured cells derived from the outflow region of the eye in primary open angle glaucoma (POAG). This model is used in this example and is discussed generally in an article entitled "5-beta-dihydrocortisol: Possible Mediator of the Ocular Hypertension in Glaucoma," *Investigative Ophthalmology & Visual Science*, March 1985, Vol. 26., pp. 393-395, which is incorporated herein by reference.

As shown below, 3-alpha, 5-beta-tetrahydrocortisol, a cortisol metabolite, previously considered to be biologically inactive, surprisingly lowers the IOP of rabbits made ocular hypertensive with the combination of dexamethasone and 5-beta-dihydrocortisol.

Young New Zealand white rabbits weighing less than 2 Kg were used as the test animals. The animals were treated by placing 25 $\mu$l of the test solution on each eye four times a day, seven days a week. IOP was measured several times a week between 8:00 to 10:00 a.m. with an Alcon pneumotonometer (O.C.V.M. from Digilab Division of Bio-Rad) after addition of a topical anesthetic (tetracaine). A single mean value was used for each animal. Each group contained 6 animals and the data reported are the mean IOP of each group. The steroids were suspended in phosphate buffered saline (PBS) by homogenization with a Teflon pestle. This produced a fine suspension of the steroids that minimized corneal irritation. The experiments were carried out in a masked fashion.

FIG. 1 shows the average IOP data of animals receiving 0.06% dexamethasone plus 0.1% 5-beta-dihydrocortisol and PBS (vehicle control) for from 23 days to 32 days.

Animals treated with the steroid mixtures responded with an increase IOP of approximately 6 mmHg within seven to ten days. This is similar to findings reported previously. On day 23 of the experiment the animals receiving the steroid mixture were divided into three groups, one group continued to receive the dexamethasone and 5-beta-dihydrocortisol in both eyes (black dots), the second group received 1% 3-alpha, 5-beta-tetrahydrocortisol (circles) along with the same amount of dexamethasone and 5-beta-dihydrocortisol and in the third group all treatment was discontinued (triangles). The animals in the last two groups responded with a decrease in IOP of about 5 mmHg, beginning on the seventh day of the new medication regimen. The line represented with squares as the points of data is a control solution of PBS only.

In three separate experiments where 3-alpha, 5-beta-tetrahydrocortisol was added to dexamethasone plus 5-beta-DHF on days 16, 20 and 23 of therapy, the groups receiving the invention tetrahydrocortisol (I) responded with a significant lowering of IOP of 3 to 5 mmHG ($p < 0.05$). The ocular hypotensive effect appeared within five to seven days after (I) was started and persisted throughout the duration of the experiments.

As earlier mentioned, it is believed that tetrahydrocortisol (I) may function by competitively inhibiting A-ring reductase activity. Thus, other A-ring reductase inhibitors may also function effectively in a treating composition of this invention. Examples of such include progesterone and testosterone. The dosage levels and treating method are as earlier described for tetrahydrocortisol (I).

It is to be understood that the active drug, such as tetrahydrocortisol (I) may be administered itself or in the form of an opthalmically acceptable salt form of the compound or any other suitable form which does not destroy the topical activity of the active drug.

What is claimed is:

1. A method of controlling intraocular pressure comprising topically administering to an affected eye a composition containing as an active agent an intraocular pressure lowering effective amount of tetrahydrocortisol, or an ophthalmically acceptable salt form thereof.

2. A method of claim 1 wherein said tetrahydrocortisol is the 3-alpha, 5-beta-tetrahydrocortsiol stereoisomer.

3. The method of claim 1 wherein the amount of tetrahydrocortisol is from about 0.05% by weight to about 5.0% by weight.

4. The method of claim 1 wherein the amount of tetrahydrocortsiol is from about 0.5% by weight of about 3.0% by weight.

5. A method of controlling intraocular pressure comprising topically administering to an affected eye an intraocular pressure lowering effective amount of an A-ring delta-4-reductase inhibitor or an ophthalmically acceptable salt form thereof.

6. The method of claim 5 wherein the A-ring delta-4-reductase inhibitor is progesterone.

7. The method of claim 6 wherein the A-ring delta-4-reductase inhibitor is testosterone.

* * * * *